United States Patent
Dammalapati et al.

(10) Patent No.: US 9,834,577 B2
(45) Date of Patent: Dec. 5, 2017

(54) PROCESS FOR THE PREPARATION OF GEMCITABINE-[PHENYL(BENZOXY-L-ALANINYL)] PHOSPHATE

(71) Applicants: NuCana Biomed Limited, Camberley (GB); Laurus Labs Private Ltd., Hyderabad (IN)

(72) Inventors: Venkata Lakshmi Narasimha Rao Dammalapati, Hyderabad (IN); Mani Bushan Kotala, Hyderabad (IN); Shankar Madhavaram, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 0 days.

(21) Appl. No.: 15/411,409

(22) PCT Filed: Jul. 22, 2015

(86) PCT No.: PCT/GB2015/052110
§ 371 (c)(1),
(2) Date: Jan. 20, 2017

(87) PCT Pub. No.: WO2016/012781
PCT Pub. Date: Jan. 28, 2016

(65) Prior Publication Data
US 2017/0166602 A1  Jun. 15, 2017

(30) Foreign Application Priority Data

Jul. 22, 2014 (IN) .............................. 3585/CHE/2014
Aug. 21, 2014 (GB) .................................... 1414880.3

(51) Int. Cl.
*C07H 19/10* (2006.01)
*C07H 1/02* (2006.01)

(52) U.S. Cl.
CPC ............... *C07H 19/10* (2013.01); *C07H 1/02* (2013.01)

(58) Field of Classification Search
CPC .................................. C07H 19/10; C07H 1/02
See application file for complete search history.

(56) References Cited

FOREIGN PATENT DOCUMENTS

WO  WO-2005/012327 A2  2/2005
WO  WO-2014/076490 A1  5/2014

OTHER PUBLICATIONS

International Search Report and Written Opinion dated Sep. 16, 2015, from corresponding International application No. PCT/GB2015/052110.
Slusarczyk, Magdalena et al., "Application of ProTide Technology to Gemcitabine: A Successful Approach to Overcome the Key Cancer Resistance Mechanisms Leads to a New Agent (NUC-1031) in Clinical Development," Journal of Medicinal Chemistry vol. 57, No. 4, Feb. 27, 2014, pp. 1531-1542.
Search Report issued by the Intellectual Property Office in corresponding Application No. GB1414880.3, dated Apr. 20, 2015.

*Primary Examiner* — Kahsay Habte
(74) *Attorney, Agent, or Firm* — Foley Hoag LLP

(57) ABSTRACT

The present invention provides a process for the preparation of gemcitabine-[phenyl(benzoxy-L-alaninyl)] phosphate of Formula I in high yield and purity.

19 Claims, No Drawings

PROCESS FOR THE PREPARATION OF GEMCITABINE-[PHENYL(BENZOXY-L-ALANINYL)] PHOSPHATE

RELATED APPLICATIONS

This application is a §371 national stage application based on Patent Cooperation Treaty Application serial number PCT/GB2015/052110, filed Jul. 22, 2015, which claims the benefit of priority to GB 1414880.3, filed Aug. 21, 2014; and IN 3585/CHE/2014, filed Jul. 22, 2014.

FIELD OF THE INVENTION

The present invention generally relates to gemcitabine phosphoramidate derivatives, processes for its preparation and pharmaceutical compositions containing the same.

BACKGROUND OF THE INVENTION

A number of nucleoside analogs such as cytarabine, fludarabine, cladribine, capecitabine, gemcitabine and pentostatin are used clinically as highly effective anti-neoplastic agents. Among these, gemcitabine (2',2'-difluoro-2'-deoxy-cytidine, Gemzar™ is of particular interest due to its unique activity against solid tumors and is presently used therapeutically to treat bladder, breast, lung, ovarian and pancreatic cancer.

Several self-potentiating mechanisms unique to this nucleoside analog are believed responsible for the activity of gemcitabine against solid tumors. The diphosphate metabolite of gemcitabine inhibits ribonucleotide reductase, which results in lower concentrations of intracellular deoxycytidine triphosphate (dCTP) and thus, increased incorporation of the triphosphate gemcitabine metabolite into DNA, which results in inhibition of DNA synthesis and blocks completion of the cell division cycle. Additionally, reduction in dCTP concentration up regulates the enzyme cytidine kinase, which is responsible for initial phosphorylation of gemcitabine, a necessary step in the inhibition of DNA synthesis by the drug. Finally, the triphosphate metabolite of gemcitabine is an inhibitor of cytidine deaminase, which is responsible for gemcitabine inactivation by conversion to the uridine metabolite. Accordingly, the additive nature of the above factors may explain the efficacy of gemcitabine in treating solid tumors.

Due to the lipophilic nature of the ProTides, these molecules can deliver nucleoside monophosphates directly in to the intact tumor cell. Previous studies have characterized multiple cellular transport mechanisms for nucleoside analog drugs and their derivatives (for a review, see Balimane et al., Adv. Drug Delivery Rev. 1999, 39, 183-209). A relatively hydrophilic compound, gemcitabine has limited ability to permeate plasma membranes via passive diffusion and several studies have demonstrated that gemcitabine is a substrate for equilibrative and concentrative nucleoside transporters (ENT's and CNT's respectively). Specifically, gemcitabine is transported by human ENT1, ENT2, CNT1 and CNT3, but not the purine-selective concentrative transporter CNT2 (see Mackey et al., Cancer Res. 1998, 58, 4349-4357; Mackey et al., J. Natl. Cancer Inst. 1999, 91, 1876-1881; and Fang et al., Biochem. J. 1996, 317, 457465).

U.S. Pat. No 4,808,614 discloses 2,2'-difluoronucleosides which are known anti-viral and anti-tumor agents, in particular 1-(2-oxo-4-amino-1H-pyrimidin-1 yl)-2-desoxy-2,2'-difluororibose (commonly known as Gemcitabine).

J. Org. Chem. Vol. 64, No. 22, 1999 disclosed a process for the selective protection of 4-NH2, 3'-OH and 5'OH positions of gemcitabine either as monoprotected or diprotected and were synthesized in good yield by employing commonly used di-tert-butyl dicarbonate. However, this publication does not provide preparation of phosphoramidate derivatives of gemcitabine and is esentially directed to PBR ligands of gemcitabine such as those having isoquinoline moiety.

U.S. Pat. No 7,951,787 discloses phosphoramidate derivatives of nucleotides such as 2'-deoxy-2',2'-difluoro-D-cytidine-5'-O-[phenyl(benzoxy-L-alaninyl)] phosphate (also referred to as gemcitabine-[phenyl(benzoxy-L-alaninyl)] phosphate of Formula I). Methods for chemically synthesizing these derivatives are disclosed in this patent by reacting gemcitabine or its structural variants with appropriate phosphochloridate in the presence of N-methylimidazole followed by purification of the product by column chromatography, eluting with dichloromethane/methanol 95:5 to give pure product as a white foamy solid with very low yield of 16%.

Formula I

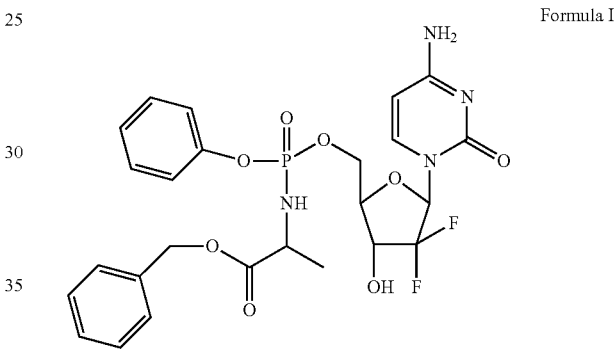

The purity and the yield of gemcitabine-[phenyl(benzoxy-L-alaninyl)] phosphate derivative as per the '787 patent are not satisfactory as starting nucleotide used in this reaction has two polar functional groups (3'-hydroxy and 4-amino), which can also form phosphoramidate ProTide esters along with 5'-hydroxy group, which is required for the formation of gemcitabine-[phenyl(benzoxy-L-alaninyl)] phosphate of Formula I. Also the said process involves the column chromatographic purification for isolating the desired compounds; such processes are tedious, labor intensive and time consuming and hence not viable for commercial scale operations. The above described process is schematically represented as follows:

-continued

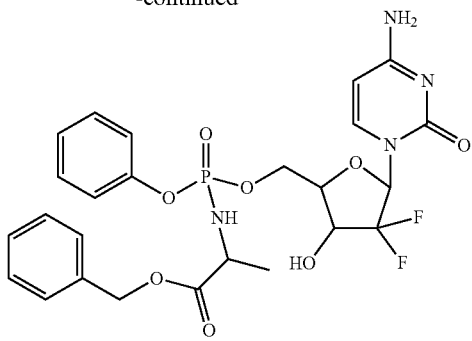

To overcome the difficulties associated with the '787 patent, the present inventors have tried an improved process for preparing gemcitabine phosphoramidate ProTides such as gemcitabine-[phenyl(benzoxy-L-alaninyl)] phosphate, wherein only 3'-hydroxy protected gemcitabine is used as starting material for coupling with ProTide intermediate using either N-methyl imidazole (NMI) or t-butyl magnesium halide (Br or Cl) followed by deprotection and column chromatographic purification which resulted gemcitabine-[phenyl(benzoxy-L-alaninyl)] phosphate in an overall yield of 35-65%. This process resulted in a chemical purity of greater than 95% as a mixture of diastereomers and mixture of both diastereomers in approximately 2:1 ratio having around 1% of methoxy impurities. A similar process is described in Slusarczyk et al; *J. Med. Chem.;* 2014, 57, 1531-1542.

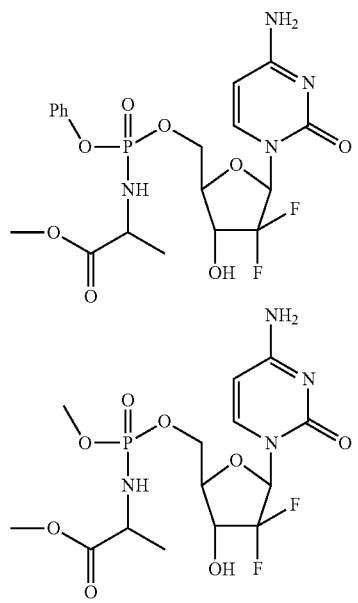

It is therefore an object of the present invention to provide a process for the preparation of gemcitabine-[phenyl(benzoxy-L-alaninyl)] phosphate) in high yield and purity. Improvements include protection of both polar functional groups (3'-hydroxy and 4-amino) of gemcitabine followed by coupling with ProTide intermediate and final deprotection to obtain gemcitabine-[phenyl(benzoxy-L-alaninyl)] phosphate with higher overall yield and purity of about 80-90%; it is evident that the new process represents a valuable alternative to the direct coupling of mono-protected gemcitabine with ProTide (35-65% yield).

SUMMARY OF THE INVENTION

The present invention encompasses a process for the preparation of gemcitabine-[phenyl(benzoxy-L-alaninyl)] phosphate derivative in high yields and purity.

In a first aspect of the invention is provided a process for the preparation of gemcitabine-[phenyl(benzoxy-L-alaninyl)] phosphate of Formula I, Formula I

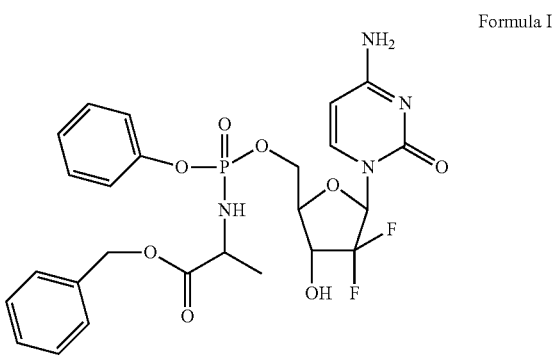 [SMILES: CC(NP(=O)(OCC1OC(n2ccc(N)nc2=O)C(F)(F)C1O)Oc1ccccc1)C(=O)OCc1ccccc1]

comprising:
a) reacting a protected gemcitabine derivative of Formula IV

Formula IV

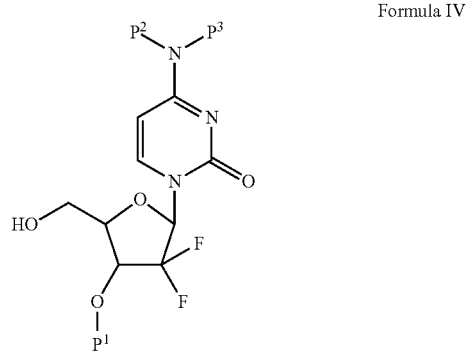

wherein $P^1$ is a hydroxy protecting group; $P^2$ represents an amine protecting group; and $P^3$ represents a hydrogen or an amine protecting group; with ProTide intermediate of Formula III, wherein "X" is a leaving group, Formula III

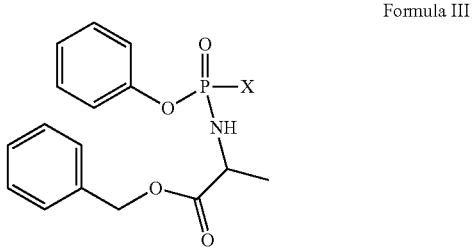

to obtain protected phosphoramidate of Formula II; and

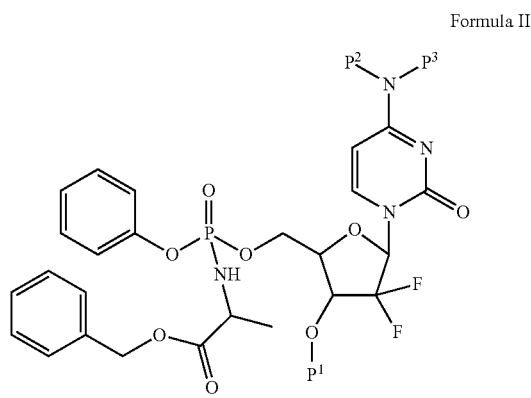

Formula II b) deprotecting the protected phosphoramidate of Formula II to obtain gemcitabine-[phenyl(benzoxy-L-alaninyl)] phosphate.

The leaving group may be selected from the group consisting of Cl, Br, I, tosylate, mesylate, trifluoroacetate, triflurosulfonate.

The hydroxy protecting group may be independently selected from optionally substituted —Si($C_{1-6}$alkyl)$_3$, optionally substituted —C(O)-$C_1$-$C_6$-alkyl, optionally substituted —C(O)-aryl, optionally substituted —C(O)—O$C_1$-$C_6$-alkyl, —C(O)—O-allyl, —C(O)—O—CH$_2$-fluorenyl, optionally substituted —CH(aryl)$_3$, optionally substituted —($C_1$-$C_3$-alkylene)-aryl, optionally substituted —C(O)OCH$_2$-aryl and —$C_1$-$C_4$-alkyl-O—$C_1$-$C_4$-alkyl.

An amino protecting group may at each occurrence be independently selected from —C(O)O$C_1$-$C_6$-alkyl, optionally substituted —C(O)OCH$_2$-aryl, —C(O)—O-allyl, —C(O)—O—CH$_2$-fluorenyl, optionally substituted —CH(aryl)$_3$, optionally substituted —($C_1$-$C_3$-alkylene)-aryl, optionally substituted —C(O)—$C_1$-$C_6$-alkyl, optionally substituted —C(O)-aryl, —S(O)$_2$-$C_1$-$C_6$-alkyl, optionally substituted —S(O)$_2$-aryl and optionally substituted —Si($C_{1-6}$ alkyl)$_3$.

In a second aspect of the invention is provided a compound of formula II. These compounds are useful intermediates in the synthesis of gemcitabine-[phenyl(benzoxy-L-alaninyl)] phosphate.

In a third aspect of the invention is provided a process for the preparation of gemcitabine-[phenyl(benzoxy-L-alaninyl)] phosphate of Formula I,

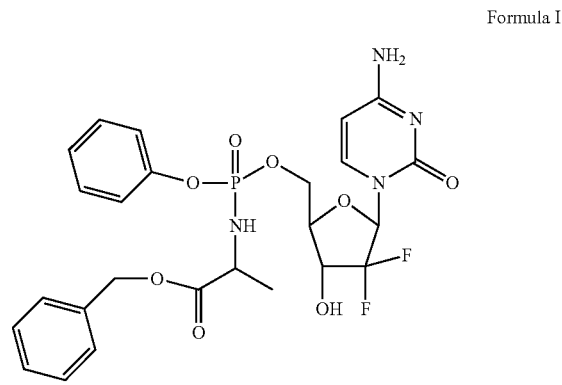 [SMILES: CC(NP(=O)(OCC1OC(n2ccc(N)nc2=O)C(F)(F)C1O)Oc1ccccc1)C(=O)OCc1ccccc1]

Formula I comprising:
a) deprotecting the protected phosphoramidate of Formula II to obtain gemcitabine-[phenyl(benzoxy-L-alaninyl)] phosphate of Formula I.

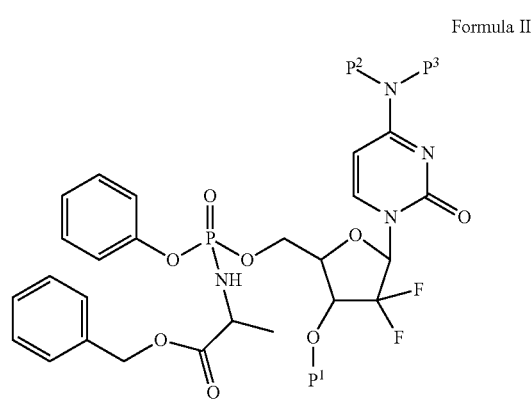

Formula II

In a fourth aspect of the invention is provided gemcitabine-[phenyl(benzoxy-L-alaninyl)] phosphate made according to the processes of the invention. Likewise, the present invention provides a pharmaceutical composition and methods to treat or prevent diseases or disorders such as cancer using gemcitabine phosphoramidate derivatives prepared by the processes of the invention.

DETAILED DESCRIPTION OF THE INVENTION

The present invention provides a process for the preparation of gemcitabine-[phenyl(benzoxy-L-alaninyl)] phosphate.

In accordance with a first embodiment, the present invention provides a process for the preparation of gemcitabine-[phenyl(benzoxy-L-alaninyl)] phosphate of Formula I,

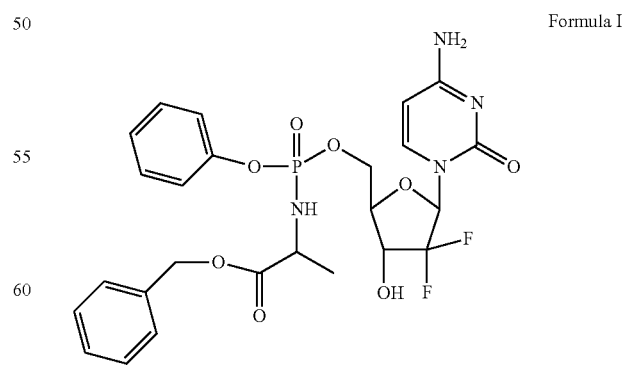

Formula I comprising:
a) reacting protected gemcitabine derivative of Formula IV

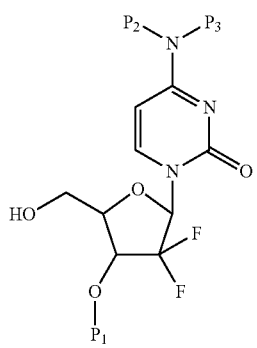

Formula IV wherein P¹ is a hydroxy protecting group; P² represents an amine protecting group; and P³ represents a hydrogen or an amine protecting group; with ProTide intermediate of Formula III, wherein "X" is a leaving group,

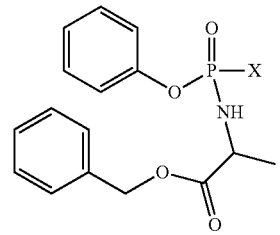

Formula III to obtain protected phosphoramidate of Formula II

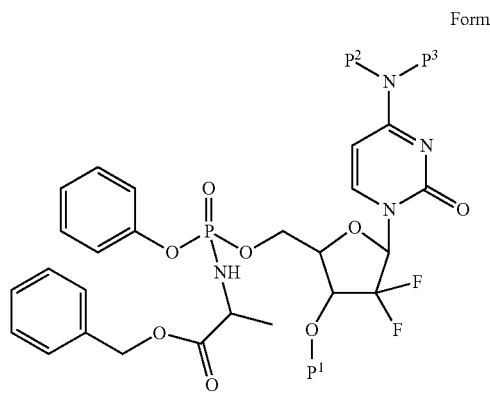

Formula II b) deprotecting the protected phosphoramidate of Formula II to obtain gemcitabine-[phenyl(benzoxy-L-alaninyl)] phosphate.

Many of the bis protected starting compounds of Formula IV are known in the art and can be prepared by any known methods. For example starting compounds of Formula IV may be synthesized from gemcitabine by protecting the 3'-hydroxy and 4-amino groups with suitable protecting groups. The protecting groups can typically be added and removed using conventional protecting group methodology, for example, as described in "Protective Groups in Organic Chemistry," edited by J W F McOmie (1973); "Protective Groups in Organic Synthesis," $2^{nd}$ edition, T W Greene (1991); and "Protecting Groups", $3^{rd}$ addition P. J Koscienski (1995).

It will typically be necessary to prepare the 3'-hydroxy and 4-amino group protected compounds by first protecting the 5'-hydroxy group of gemcitabine with a protecting group which is orthogonal to those which will be used to protect the 3'-hydroxy and 4-amino group (i.e. a group which can be removed without also removing the desired 3'-hydroxy and 4-amino groups). Simultaneously or subsequently, the 3'-hydroxy and 4-amino groups are protected with the desired protecting group(s) and the 5'-hydroxy protecting group can be removed to generate the compound of formula II. Certain protecting groups can be simultaneously introduced onto the 3'-hydroxy and 5'-hydroxy and optionally the 4-amino groups and then selectively removed from the 5' hydroxyl group without being removed from the 3'-hydroxy and, if present, the 4-amino group.

The ProTide intermediate of Formula III is known in the art, for example the ProTide intermediate of Formula III can be obtained according to U.S. Pat. No 7,951,787.

According to some embodiments, the leaving group "X" is selected from the group consisting of Cl, Br, I, tosylate, mesylate, trifluoroacetate, triflurosulfonate. Preferably X is Cl.

According to some embodiments, P¹ is independently selected from optionally substituted —Si($C_{1-6}$alkyl)$_3$, optionally substituted —C(O)—$C_1$-$C_6$-alkyl, optionally substituted —C(O)-aryl, optionally substituted —C(O)—O$C_1$-$C_6$-alkyl, —C(O)—O-allyl, —C(O)—O—$CH_2$-fluorenyl, optionally substituted —CH(aryl)$_3$, optionally substituted —($C_1$-$C_3$-alkylene)-aryl, optionally substituted —C(O)O$CH_2$-aryl and —$C_1$-$C_4$-alkyl-O—$C_1$-$C_4$-alkyl.

P¹ may be independently selected from optionally substituted —Si($C_{1-6}$alkyl)$_3$, optionally substituted —C(O)—O$C_1$-$C_6$-alkyl and optionally substituted —C(O)O$CH_2$-aryl, —C(O)—O—allyl. Preferably, P¹ is selected from —C(O)O-tBu, —C(O)O-benzyl and —C(O)O$CH_2$-allyl. Thus, P¹ may be —C(O)O$CH_2$-aryl.

Alternatively, P¹ may be independently selected from optionally substituted —C(O)—$C_1$-$C_6$-alkyl and optionally substituted —C(O)-aryl, e.g. P¹ may be independently selected from benzoyl and acetyl.

P² may be independently selected from —C(O)O$C_1$-$C_6$-alkyl, optionally substituted —C(O)O$CH_2$-aryl, —C(O)—O-allyl, —C(O)—O—$CH_2$-fluorenyl, optionally substituted —CH(aryl)$_3$, optionally substituted —($C_1$-$C_3$-alkylene)-aryl, optionally substituted —C(O)—$C_1$-$C_6$-alkyl, optionally substituted —C(O)-aryl, —S(O)$_2$—$C_1$-$C_6$-alkyl, optionally substituted —S(O)$_2$-aryl and optionally substituted —Si($C_{1-6}$alkyl)$_3$.

P² may be independently selected from —C(O)O$C_1$-$C_6$-alkyl, optionally substituted —C(O)O$CH_2$-aryl, —C(O)—O-allyl, optionally substituted —CH(aryl)$_3$, and optionally substituted —Si($C_{1-6}$alkyl)$_3$. Preferably, P² is selected from —C(O)O-tBu, —C(O)O-benzyl and —C(O)O$CH_2$-allyl. Thus, P² may be —C(O)O$CH_2$-aryl.

Alternatively, P² may be independently selected from optionally substituted —C(O)—$C_1$-$C_6$-alkyl and optionally substituted —C(O)-aryl, e.g. P² may be independently selected from benzoyl and acetyl.

Likewise, P³ may be independently selected from H, —C(O)O$C_1$-$C_6$-alkyl, optionally substituted —C(O)O$CH_2$-aryl, —C(O)—O-allyl, —C(O)—O—$CH_2$-fluorenyl, optionally substituted —CH(aryl)$_3$, optionally substituted —($C_1$-$C_3$-alkylene)-aryl, optionally substituted —C(O)—$C_1$-$C_6$-alkyl, optionally substituted —C(O)-aryl, —$S(O)_2$—$C_1$-$C_6$-alkyl, optionally substituted —$S(O)_2$-aryl and optionally substituted —Si($C_{1-6}$alkyl)$_3$.

Preferably, $P^3$ is H.

The group optionally substituted —Si($C_{1-6}$alkyl)$_3$ may be a —Si($C_{1-4}$ alkyl)$_3$ group. The group is (i.e. the alkyl groups are) preferably unsubstituted. Illustrative examples include triethylsilyl and t-butyl-dimethylsilyl.

The group optionally substituted —C(O)—$C_1$-$C_6$-alkyl may be a —C(O)—$C_1$-$C_6$-alkyl group. The group (i.e. the alkyl group) is preferably unsubstituted. Illustrative examples include acetyl and propionyl.

The group optionally substituted —C(O)-aryl may be a —C(O)-phenyl group. The group (i.e. the phenyl group) is preferably unsubstituted. Illustrative examples include benzoyl.

The group optionally substituted —C(O)—O$C_1$-$C_6$-alkyl may be a —C(O)—O$C_1$-$C_4$-alkyl group. The group (i.e. the alkyl group) is preferably unsubstituted. Illustrative examples include —C(O)—O-methyl and —C(O)—O-ethyl. A particularly preferred example is C(O)OtBu.

The group optionally substituted —($C_1$-$C_3$-alkylene)-aryl is preferably an optionally substituted benzyl group. Illustrative examples include benzyl, phenethyl, 4-methoxy benzyl, 4-nitrobenzyl, 4-bromobenzyl, 2,3-dimethoxybenzyl and 2,4-dimethoxybenzyl.

The group optionally substituted —C(O)OCH$_2$-aryl is preferably an optionally substituted —C(O)Obenzyl group. Illustrative examples include —C(O)Obenzyl and —C(O)O-(4-methoxybenzyl).

The group optionally substituted —$C_1$-$C_4$-alkyl-O—$C_1$-$C_4$-alkyl may be a —$C_1$-$C_2$-alkyl-O—$C_1$-$C_2$-alkyl group. The group is (i.e. the alkyl groups are) preferably unsubstituted. Illustrative examples include methoxy-methyl (MOM) and 2-methoxy-ethoxy-methyl (MEM).

The group optionally substituted —$S(O)_2$—$C_1$-$C_6$-alkyl may be a —$S(O)_2$—$C_1$-$C_4$-alkyl group. The group (i.e. the alkyl group) is preferably unsubstituted. Illustrative examples include methanesulfonate.

The group optionally substituted —$S(O)_2$-aryl may be a —$S(O)_2$-phenyl group. Illustrative examples include phenylsulfonate, 4-methylphenylsulfonate and 4-nitro phenylsulfonate.

The group optionally substituted —CH(aryl)$_3$ may be a —CH(phenyl)$_3$ group. Illustrative examples include trityl.

The deprotection step may comprise two individual deprotection reactions. This is the case where two different protecting groups are used and where those two protecting groups cannot be removed under the same conditions.

Preferably, however, the deprotection step comprises a single deprotection reaction in which both protecting groups are removed. Thus, preferably, $P^1$ and $P^2$ are protecting groups which can be removed under the same conditions. Preferably, $P^1$ and $P^2$ are the same.

It may be that both $P^1$ and $P^2$ are a group selected from optionally substituted —C(O)O$C_1$-$C_6$-alkyl, —C(O)—O-allyl and optionally substituted —C(O)OCH$_2$-aryl. Thus, both $P^1$ and $P^2$ may be a group selected from C(O)OtBu, —C(O)—O-allyl and C(O)O-benzyl. In a preferred embodiment, $P^1$ and $P^2$ are both C(O)OtBu groups.

Preferably $P^3$ is hydrogen. Thus, in a preferred embodiment, $P^1$ and $P^2$ are the same groups and $P^3$ is hydrogen. Thus, in a particularly preferred embodiment, $P^1$ and $P^2$ are both C(O)OtBu groups and $P^3$ is hydrogen.

Any of the aforementioned alkyl and aryl (e.g. phenyl, including the phenyl groups in benzyl groups) groups, are optionally substituted, where chemically possible, by 1 to 3 substituents which are each independently at each occurrence selected from the group consisting of: oxo, =NR$^a$, =NOR$^a$, halo, nitro, cyano, NR$^a$ R$^1$, NR$^a$S(O)$_2$R$^a$, NR$^a$-CONR$^a$R$^a$, NR$^a$CO$_2$R$^a$, OR$^a$; SR$^a$, SOR$^a$, SO$_3$R$^a$, SO$_2$R$^a$, SO$_2$NR$^a$R$^a$, CO$_2$R$^a$ C(O)R$^a$, CONR$^a$R$^a$, $C_1$-$C_4$-alkyl, $C_2$-$C_4$-alkenyl, $C_2$-$C_4$-alkenyl, and $C_1$-$C_4$ haloalkyl; wherein R$^a$ is independently at each occurrence selected from H, $C_1$-$C_4$ alkyl and $C_1$-$C_4$ haloalkyl. It may be that any of the aforementioned alkyl groups is unsubstituted.

It may be that any of the aforementioned aryl groups (e.g. phenyl, including the phenyl groups in benzyl groups) is optionally substituted, where chemically possible, by 1 to 3 substituents which are each independently at each occurrence selected from the group consisting of: halo, nitro, cyano, NR$^a$R$^a$, NR$^a$S(O)$_2$R$^a$, NR$^a$CONR$^a$R$^a$, NR$^a$CO$_2$R$^a$, OR$^a$; SR$^a$, SOR$^a$, SO$_3$R$^a$, SO$_2$R$^a$, SO$_2$NR$^a$R$^a$, CO$_2$R$^a$ C(O) R$^a$, CONR$^a$R$^a$, $C_1$-$C_4$-alkyl, $C_2$-$C_4$-alkenyl, $C_2$-$C_4$-alkenyl, and $C_1$-$C_4$ haloalkyl; wherein R$^a$ is independently at each occurrence selected from H, $C_1$-$C_4$ alkyl and $C_1$-$C_4$ haloalkyl.

It may be that any of the aforementioned aryl (e.g. phenyl, including the phenyl groups in benzyl groups) groups is optionally substituted by 1 to 3 substituents which are each independently at each occurrence selected from the group consisting of: halo, nitro, OR$^a$; $C_1$-$C_4$-alkyl, $C_1$-$C_4$ haloalkyl; wherein R$^a$ is independently at each occurrence selected from H, $C_1$-$C_4$ alkyl and $C_1$-$C_4$ haloalkyl.

Aryl groups have from 6 to 20 carbon atoms as appropriate to satisfy valency requirements. Aryl groups are carbocyclic groups which satisfy the Huckel rule (i.e. they contain a carbocyclic ring system containing 2(2n+1)π (electrons). Aryl groups may be optionally substituted phenyl groups, optionally substituted biphenyl groups, optionally substituted naphthalenyl groups or optionally substituted anthracenyl groups. Equally, aryl groups may include non-aromatic carbocyclic portions. Preferably an aryl group is an optionally substituted phenyl group.

Alkyl groups may be straight chain or branched. Thus, for example, a $C_4$ alkyl group could be n-butyl, i-butyl or t-butyl.

In an embodiment, the present invention provides a process for the preparation of gemcitabine-[phenyl(benzoxy-L-alaninyl)] phosphate of Formula I from 3'-hydroxy and 4-amino protected gemcitabine derivatives of Formula IV, wherein the 3'-hydroxy and 4-amino groups are prior protected with t-butoxy carbonyl group, before the reaction it with ProTide intermediate of Formula III.

The step a) of the process of the first aspect may be conducted in the presence of a base. The base might be a nitrogen base. Nitrogen bases include N-alkylimidazoles, (e.g. N-methyl imidazole (NMI), imidazole, optionally substituted pyridines, (e.g. collidine, pyridine, 2,6-lutidine) and trialkylamines (e.g. triethylamine, and diisopropylethylamine). Alternatively, the base may be a Grignard reagent (i.e. an alkylmagnesium halide). Exemplary Grignard reagents include t-butylmagnesium halides such as tBuMgCl, tBuMgBr. Preferably, the base is tBuMgCl.

One of the benefits of the processes of the invention is that the introduction of the ProTide group to the 5' position of the gemcitabine can be conducted in a broader range of conditions (e.g. a greater range of bases), thus allowing the variation of this key step in the synthesis of gemcitabine-[phenyl(benzoxy-L-alaninyl)] phosphate. The ability to vary the reaction conditions more broadly allows the overall process to be optimized and, in particular, increases the likelihood that an aceonomically favourable scale-up process can be developed.

The following bases work in the reaction of step a) of the first aspect but are less preferred: triethylamine, $Na_2CO_3$, NaH.

Step a) of the first aspect may be conducted in an organic solvent. Organic solvents include but are not limited to ethers (e.g. tetrahydrofuran, dioxane, diethyl ether); ketones (e.g. acetone and methyl isobutyl ketone); halogenated solvents (e.g. dichloromethane, chloroform and 1,2-dichloroethane); and amides (e.g. DMF, NMP); or mixtures thereof. Where step a) is conducted in the presence of a Grignard reagent, the organic solvent is preferably an ether. Most preferably, the solvent is tetrahydrofuran.

Where step a) of the first aspect is conducted in the present of a nitrogen base, the organic solvent is most preferably a halogenated solvent or an amide.

The reaction is typically conducted at a suitable temperature, e.g from about-5° C. to about 40° C. Preferably, the reaction temperature is about 25° C. to about 30° C. The reaction may be allowed to stir for a period of time from about 15 mins to about 16 h and preferably from about 30 mins to about –60 mins.

The resultant organic layer containing protected phosphoramidate of Formula II can be processed directly in the same reaction vessel to form gemcitabine-[phenyl(benzoxy-L-Alaninyl)] phosphate of Formula I. Alternatively, the solvent from the organic layer may be concentrated to obtain a crude product residue by any method known in the art, at the end of the reaction, for example distillation, evaporation, rotational drying (such as with the Buchi rotary evaporator), freeze drying, fluidized bed drying, flash drying, spin flash drying, Preferably the solvent is removed by distillation under vacuum.

The processes of the invention also involve deprotection of the hydroxy and amino protecting groups.

Where a protecting group is acid sensitive, e.g. trityl, C(O)OtBu, MOM, MEM, 2,4-dimethoxybenzyl, 2,3-dimethoxybenzyl, the deprotection step can be conducted using a suitable acid. The acid may be a Bronsted acid (e.g. TFA, phosphoric acid, HCl, or formic acid) or a Lewis acid (e.g. $ZnBr_2$, CeCl3). Lewis acids (e.g. $ZnBr_2$) are less preferred. HC1 is likewise less preferred. Preferably, the acid is TFA.

Where a protecting group is base sensitive, e.g. acetyl, benzoyl, the deprotection step can be conducted using a suitable base, e.g. aqueous $NH_3$ or aqueous NaOH. Base sensitive groups may be less preferred.

Where a protecting group is a silyl group (e.g. triethylsilyl or t-butyldimethylsilyl, the deprotection step can be conducted using a suitable acid (e,g, TFA) or using a suitable fluorine source (e.g. tetrabutylammonium fluoride, fluorosilicic acid, HF). Where a protecting group is a benzyl group or a C(O)Obenzyl group, the deprotction step can be conducted using $H_2$ and a suitable catalyst (e.g. Pd/C). Such protecting groups may be less preferred.

Where a protecting group is a 4-methoxy benzyl, 2,3-dimethoxybenzyl, 2,4-dimethoxybenzyl or C(O)O-(4-methoxybenzyl) the deprotection step can be performed using a suitable oxidizing agent (e.g. meta-chloroperbenzoic acid).

Where a protecting group is —C(O)—O-allyl, the deprotection step can be performed using (PPh3)4Pd.

Where a protecting group is —C(O)—O—$CH_2$-fluorenyl, the deprotection step can be performed using piperidine.

The deprotection step may be conducted in an organic solvent or a mixture thereof. Exemplary organic solvents include, but are not limited to halogenated solvents (e.g. dichloromethane, chloroform, dichloroethane); alcohols (e.g. methanol, ethanol, isopropanol) and ethers (e.g. tetrahydrofuran, diethyl ether).

Where the deprotection step is carried out in the presence of an acid (e.g. TFA, the organic solvent is preferably a halogenated solvent, e.g. dichloromethane.

The deprotection reaction may be carried out at a temperature in the range of, for example –10° C. to about 30° C., e.g. to about 10° C. A convenient temperature to carry out the reaction is –5° C. to 5° C. The reaction may be allowed to stir for a period of time from about 15 mins to about 16 hours and preferably from about 1 hour to about 4 hours, and more preferably from about 2 hours to about 3 hours.

Where, the deprotection is performed in the presence of an acid (e.g. TFA), isolation of the product obtained after the deprotection is typically done by quenching the excess acid used in deprotection step and extracting the product with a water immiscible organic solvent and recovering the product by evaporation of the organic solvent.

Examples of water immiscible organic solvents useful in extraction include esters such as ethyl acetate, methyl acetate, isopropyl acetate and the like; chlorinated solvents such as dichloromethane, chloroform and the like; aromatic hydrocarbon solvents such as toluene, xylene and the like; preferably ethyl acetate.

Preferably, $P^1$ and $P^2$ are both C(O)OtBu groups and $P^3$ is hydrogen, step a) is carried out in the presence of tBuMgCl (e.g. in THF), and step b) is carried out using TFA (e.g. in DCM). This reaction sequence appears to provide the highest yields and HPLC purities of those assayed.

In another embodiment, the present invention provides gemcitabine-[phenyl(benzoxy-L-alaninyl)] phosphate of Formula I, obtained by the process described herein as a mixture of diastereomers in around 90% yield, with a chemical purity of at least about 98% as measured by HPLC, preferably at least about 99% as measured by HPLC as a mixture of diasteromers in approximately 1:1 ratio; and substantially free of methoxy impurities.

As used herein, the term "substantially free" refers to gemcitabine-[phenyl(benzoxy-L-Alaninyl)] phosphate of Formula I having less than the detectable levels of its methoxy impurities as measured by HPLC, preferably less than 0.01% of its methoxy impurities as measured by HPLC.

It has been observed that due to protection of both the polar functional groups (3'-hydroxy and 4-amino) of gemcitabine prior to the introduction of ProTide intermediate of Formula III, the yield and purity of the resulting gemcitabine-[phenyl(benzoxy-L-alaninyl)] phosphate is substantially enhanced. In contrast, substantially lower yields and low purities were obtained when the same reaction was performed with either no protection or partial protection of such protecting groups, as process described in the reported literature.

In certain embodiments, it may still be desirable to purify the gemcitabine-[phenyl(benzoxy-L-alaninyl)] phosphate obtained from the process of the invention. Methods of purification are well known to those skilled in the art and include chromatography (e.g. column chromatography), recrystallisation and distillation. In other embodiments, no purification is necessary.

The following abbreviations are used throughout this specification:

DCM—dichloromethane
DMF—N,N-dimethylformamide
IPA—isopropyl alcohol
NMP—N-methylpyrroldinone
TEA—triethylamine
THF—tetrahydrofuran
DIPE—diisopropylether
DMSO—dimethylsulfoxide
MTBE—methyl-t-butylether
TBDMS—tert-butyldimethylsilyl
TFA—trifluoroacetic acid

EXAMPLES

The present invention is further illustrated by the following examples, which are provided by way of illustration only and should not be construed to limit the scope of the invention.

Example 1

Protection of the 3' position—preparation of 3'-O-(tert-Butoxycarbonyl) gemcitabine.

To a stirred mixture of gemcitabine hydrochloride (50 gms) in DM water (200 ml) and dioxane (800 ml) was added $K_2CO_3$ (115.3 gms; 0.835 mol) followed by Boc anhydride (58.3 gms, 0.267 mol) at 25-30° C. and the resulting mixture was stirred at the same temperature for 48 hrs. After reaction completion, DM water (600 ml) was added and the reaction mixture was extracted with EtOAc (750 ml). The organic layer was separated, dried over $Na_2SO_4$, and concentrated to dryness under reduced pressure. The residue was cooled to 25-30° C. and treated with acetone (150 ml) and distilled under reduced pressure. Further the obtained residue was slurried from a mixture of acetone and heptane followed by DCM to obtain the title compound (51.5 gms; 85%). Purity by HPLC: 93%.

Example 2

Protection of the 3' position—preparation of 4-N-3'-O-Bis(tert-Butoxycarbonyl) gemcitabine.

To a stirred solution of 3'-O-(tert-Butoxycarbonyl) gemcitabine (25 gms) in dioxane (375 ml) was added Boc anhydride (75 gms, 0.344 mol) at 25-30° C. The reaction mixture was maintained at 40-45° C. for 90 hrs. After reaction completion, DM water (300 ml) was added; the mixture was extracted with EtOAc (375 ml). The organic layer was separated, dried over $Na_2SO_4$, and concentrated to dryness under reduced pressure. The obtained residue was cooled to 25-30° C. and slurried in EtOAc: heptane mixture to obtain the title compound (21.7 gms; 68%). Purity by HPLC: 97.09%.

Example 3

Preparation of gemcitabine-[phenyl(benzoxy-L-alaninyl)] phosphate via 4-N-3'-O-bis(tert-butoxycarbonyl) gemcitabine:

To a suspension of L-alanine benzyl ester hydrochloride (19.7 gms, 0.0914 mol) in DCM (200 ml), was charged dichloro phenyl phosphate (19.6 gms, 0.0928 mol) at 25-30° C. and cooled to −70° C. to about −75° C. TEA (18.5 gms, 0.1825 mol) was added to the reaction mixture at −70° C. to about −75° C., stirred at the same temperature for 1 hr and at 25-30° C. for 2hrs and concentrated the reaction mass under reduced pressure. The obtained residue was treated with DIPE (200 ml), filtered and concentrated under reduced pressure and stored under nitrogen at 0-7° C.

To a stirred mixture of 4-N-3'-O-bis(tert-butoxycarbonyl) gemcitabine (20 gms) in THF (200 ml), was added the ProTide intermediate prepared above taken in 200 ml THF under nitrogen atmosphere and cooled the resulting solution to −5 to 5° C. Charged 1M t-BuMgCl (10 gms, 0.0863 mol), raise the temperature to 25-30° C. and stirred for 30mins. After reaction completion the reaction mass was quenched in to water (200 ml) and extracted with EtOAc (300 ml). The organic layer was washed with 8% NaHCO3, water and finally with 20% brine solution. The organic layer separated, dried over sodium sulfate and concentrated under reduced pressure to obtain a residue.

The obtained residue was taken up in DCM (160 ml) and added TFA (160 ml) at −2 to 2° C. Maintained the reaction mass at 5-10° C. for 2-3 hrs and quenched in to 10% sodium carbonate solution (2 Lit) at below 15° C. Extracted with EtOAc (800 ml), dried the organic layer over sodium sulfate and evaporated under reduced pressure. The obtained residue was slurried in DCM: heptane mixture to obtain the title compound (21.6 gms; 85%).

Purity by HPLC: 99.68% (mixture of both diastereomers in approximately 1:1 ratio).

Comparative Example

Preparation of gemcitabine-[phenyhbenzoxy-L-alaninyl)] phosphate via 3'-monoprotected gemcitabine:

To a suspension of L-alanine benzyl ester hydrochloride (12.54 gms, 0.0583 mol) in DCM (125 ml), was charged dichloro phenyl phosphate (13.47 gms, 0.0638 mol) at 25-35° C. and cooled to −70° C. to about −78° C. TEA (11.76 gms, 0.1164 mol) was added to the reaction mixture at −70° C. to about −75° C., stirred at the same temperature for 1 hr and at 25-35° C. for 2 hrs and concentrated the reaction mass. The obtained residue was treated with MTBE (200 ml), filtered and concentrated under reduced pressure and stored under nitrogen at 2-8° C.

To a stirred mixture of 3'-O-(tert-butoxycarbonyl) gemcitabine (10 gms) in THF (250 ml), was added 1M t-BuMgCl (6.43 gms, 0.0550 mol) at 0-5° C. followed by ProTide intermediate taken in 200 ml THF under nitrogen atmosphere. Raised the temperature to 25-35° C. and stirred for 1 hr. After reaction completion, the reaction mass was quenched in to 0.5 N HCl and extracted with EtOAc (250 ml). Separated the organic layer, washed with 10% $NaHCO_3$ solution followed by 20% NaCl solution and concentrated under reduced pressure to obtain a residue.

The obtained residue was taken up in DCM (93 ml) and added TFA (42 ml) at 0-5° C. Maintained the reaction mass at 25-35° C. for 2 hrs and quenched in to 10% $NaHCO_3$ solution. Extracted with EtOAc (800 ml), washed the organic layer with 10% $NaHCO_3$ solution followed by 20% NaCl solution and thee organic layer was evaporated under reduced pressure. The crude compound was purified by column chromatography using silica gel eluting with 2.5%, 5% & 7% methanol in DCM and the obtained pure compound was purified from a mixture of ethyl acetate and heptane to obtain the title compound (10.3 gms; 64%).

Purity by HPLC: 98.24% (mixture of both diastereomers in approximately 2:1 ratio).

Thus it can be seen that the process of the invention gives a substantially improved HPLC purity relative to a corresponding route which proceeds via a mono-protected gemcitabine derivative. This represents a major advantage in scaling up the synthesis of gemcitabine-[phenyl(benzoxy-L-alaninyl)] phosphate.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

The invention claimed is:

1. A process for the preparation of gemcitabine-[phenyl(benzoxy-L-alaninyl)]phosphate of Formula I,

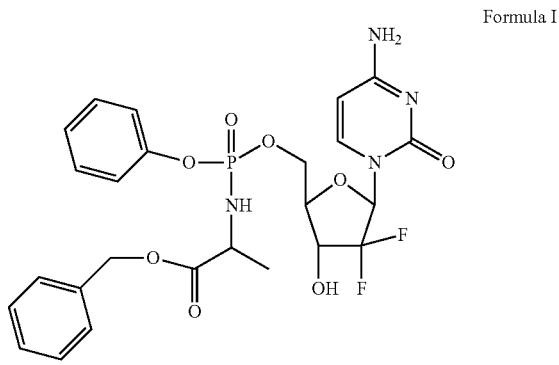 [SMILES: CC(NP(=O)(OCC1OC(n2ccc(N)nc2=O)C(F)(F)C1O)Oc1ccccc1)C(=O)OCc1ccccc1]

Formula I the process comprising:
a) reacting protected gemcitabine derivative of Formula IV

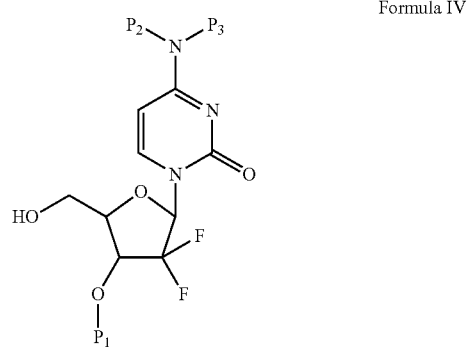

Formula IV wherein
P$^1$ is a hydroxy protecting group independently selected from the group consisting of optionally substituted —Si(C$_{1-6}$alkyl)$_3$, optionally substituted —C(O)—C$_1$-C$_6$-alkyl, optionally substituted —C(O)-aryl, optionally substituted —C(O)—OC$_1$-C$_6$-alkyl, —C(O)—O-allyl, —C(O)—O—CH$_2$-fluorenyl, optionally substituted —CH(aryl)$_3$, optionally substituted —(C$_1$-C$_3$-alkylene)-aryl, optionally substituted —C(O)OCH$_2$-aryl, and —C$_1$-C$_4$-alkyl-O—C$_1$-C$_4$-alkyl;
P$^2$ represents an amine protecting group independently selected from the group consisting of —C(O)OC$_1$-C$_6$-alkyl, optionally substituted —C(O)OCH$_2$-aryl, —C(O)—O-allyl, —C(O)—O—CH$_2$-fluorenyl, optionally substituted —CH(aryl)$_3$, optionally substituted —(C$_1$-C$_3$-alkylene)-aryl, optionally substituted —C(O)—C$_1$-C$_6$-alkyl, optionally substituted —C(O)-aryl, —S(O)$_2$—C$_1$-C$_6$-alkyl, optionally substituted —S(O)$_2$-aryl, and optionally substituted —Si(C$_{1-6}$alkyl)$_3$; and
P$^3$ represents a hydrogen or an amine protecting group independently selected from the group consisting of —C(O)OC$_1$-C$_6$-alkyl, optionally substituted —C(O)OCH$_2$-aryl, —C(O)—O-allyl, —C(O)—O—CH$_2$-fluorenyl, optionally substituted —CH(aryl)$_3$, optionally substituted —(C$_1$-C$_3$-alkylene)-aryl, optionally substituted —C(O)—C$_1$-C$_6$-alkyl, optionally substituted —C(O)-aryl, —S(O)$_2$—C$_1$-C$_6$-alkyl, optionally substituted —S(O)$_2$-aryl, and optionally substituted —Si(C$_{1-6}$alkyl)$_3$;
with ProTide intermediate of Formula III, wherein "X" is a leaving group,

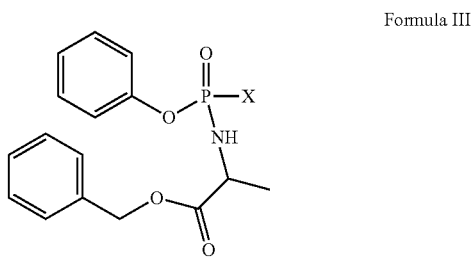

Formula III to obtain protected phosphoramidate of Formula II

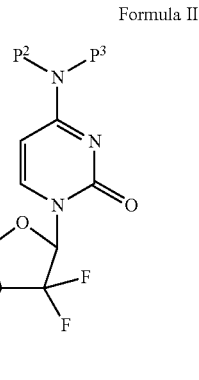

Formula II b) deprotecting the protected phosphoramidate of Formula II to obtain gemcitabine-[phenyl(benzoxy-L-alaninyl)]phosphate by exposing the phosphoramidate of Formula II to a reagent selected from the group consisting of a Bronsted acid; a Lewis acid; a base; a fluorine source; H$_2$ and a catalyst an oxidizing agent (PPh$_3$)$_4$Pd; and piperidine.

2. The process of claim 1, wherein X is selected from the group consisting of Cl, Br, I, tosylate, mesylate, trifluoroacetate, triflurosulfonate.

3. The process of claim 1, wherein step a) is conducted in the presence of a base.

4. The process of claim 3, wherein the base is tBuMgCl.

5. A process for the preparation of gemcitabine-[phenyl(benzoxy-L-alaninyl)]phosphate of Formula I, Formula I

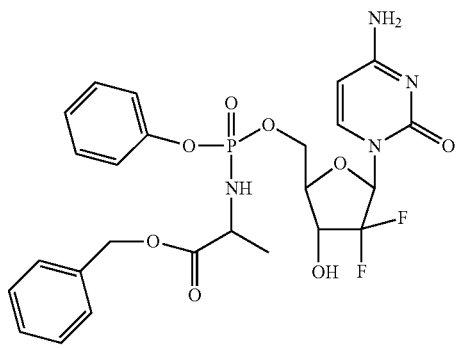

comprising:
a) deprotecting a protected phosphoramidate of Formula II to obtain gemcitabine-[phenyl(benzoxy-L-alaninyl)] phosphate of Formula I by exposing the phosphoramidate of Formula II to a reagent selected from the group consisting of a Bronsted acid; a Lewis acid; a base; a fluorine source; $H_2$ and a catalyst an oxidizing agent $(PPh_3)_4Pd$; and piperidine;

Formula II

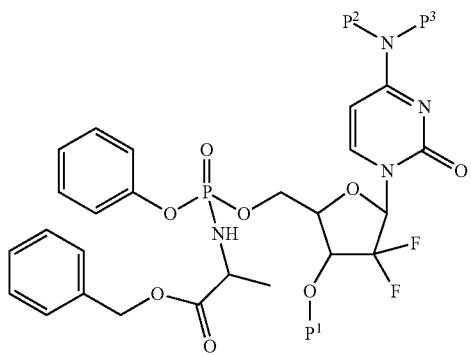

wherein
P$^1$ is a hydroxy protecting group independently selected from the group consisting of optionally substituted —Si(C$_{1-6}$alkyl)$_3$, optionally substituted —C(O)—C$_1$-C$_6$-alkyl, optionally substituted —C(O)-aryl, optionally substituted —C(O)—OC$_1$-C$_6$-alkyl, —C(O)—O-allyl, —C(O)—O—CH$_2$-fluorenyl, optionally substituted —CH(aryl)$_3$ optionally substituted —(C$_1$-C$_3$-alkylene)-aryl, optionally substituted —C(O)OCH$_2$-aryl, and —C$_1$-C$_4$-alkyl-O—C$_1$-C$_4$-alkyl;

P$^2$ represents an amine protecting group independently selected from the group consisting of —C(O)OC$_1$-C$_6$-alkyl, optionally substituted —C(O)OCH$_2$-aryl, —C(O)—O-allyl, —C(O)—O—CH$_2$-fluorenyl, optionally substituted —CH(aryl)$_3$, optionally substituted —(C$_1$-C$_3$-alkylene)-aryl, optionally substituted —C(O)—C$_1$-C$_6$-alkyl, optionally substituted —C(O)-aryl, —S(O)$_2$—C$_1$-C$_6$-alkyl, optionally substituted —S(O)$_2$-aryl, and optionally substituted —Si(C$_{1-6}$alkyl)$_3$; and P$^3$ represents a hydrogen or an amine protecting group independently selected from the group consisting of —C(O)OC$_1$-C$_6$-alkyl, optionally substituted —C(O)OCH$_2$-aryl, —C(O)—O-allyl, —C(O)—O—CH$_2$-fluorenyl, optionally substituted —CH(aryl)$_3$ optionally substituted —(C$_1$-C$_3$-alkylene)-aryl, optionally substituted —C(O)—C$_1$-C$_6$-alkyl, optionally substituted —C(O)-aryl, —S(O)$_2$—C$_1$-C$_6$-alkyl, optionally substituted —S(O)$_2$-aryl, and optionally substituted —Si(C$_{1-6}$alkyl)$_3$.

6. The process of claim 5, wherein P$^1$ is independently selected from the group consisting of optionally substituted —Si(C$_{1-6}$alkyl)$_3$, optionally substituted —C(O)—OC$_1$-C$_6$-alkyl, optionally substituted —C(O)OCH$_2$-aryl, and —C(O)—O-allyl.

7. The process of claim 5, wherein P$^1$ is C(O)—O-tBu.

8. The process of claim 5, wherein P$^2$ is independently selected from the group consisting of —C(O)OC$_1$-C$_6$-alkyl, optionally substituted —C(O)OCH$_2$-aryl, —C(O)—O-allyl, optionally substituted —CH(aryl)$_3$, and optionally substituted —Si(C$_{1-6}$alkyl)$_3$.

9. The process of claim 5, wherein P$^2$ is C(O)—O-tBu.

10. The process of claim 5, wherein P$^3$ is H.

11. The process of claim 7, wherein the deprotection step is conducted using a Bronsted acid.

12. The process of claim 11, wherein the Bronsted acid is TFA.

13. A compound of formula II

Formula II

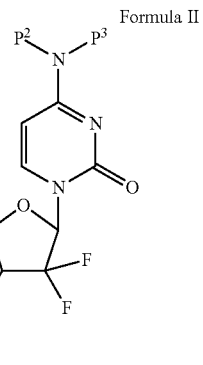

wherein
P$^1$ is a hydroxy protecting group independently selected from the group consisting of optionally substituted —Si(C$_{1-6}$alkyl)$_3$, optionally substituted —C(O)—C$_1$-C$_6$-alkyl, optionally substituted —C(O)-aryl, optionally substituted —C(O)—OC$_1$-C$_6$-alkyl, —C(O)—O-allyl, —C(O)—O—CH$_2$-fluorenyl, optionally substituted —CH(aryl)$_3$, optionally substituted —(C$_1$-C$_3$-alkylene)-aryl, optionally substituted —C(O)OCH$_2$-aryl, and —C$_1$-C$_4$-alkyl-O—C$_1$-C$_4$-alkyl;

P$^2$ represents an amine protecting group independently selected from the group consisting of —C(O)OC$_1$-C6-alkyl, optionally substituted —C(O)OCH$_2$-aryl, —C(O)—O-allyl, —C(O)—O—CH$_2$-fluorenyl, optionally substituted —CH(aryl)$_3$, optionally substituted —(C$_1$-C$_3$-alkylene)-aryl, optionally substituted —C(O)—C$_1$-C$_6$-alkyl, optionally substituted —C(O)-aryl, —S(O)$_2$—C$_1$-C$_6$-alkyl, optionally substituted —S(O)$_2$-aryl, and optionally substituted —Si(C$_{1-6}$alkyl)$_3$; and P$^3$ represents a hydrogen or an amine protecting group independently selected from the group consisting of —C(O)OC$_1$-C$_6$-alkyl, optionally substituted —C(O)OCH$_2$-aryl, —C(O)—O-allyl, —C(O)—O—CH$_2$-fluorenyl, optionally substituted —CH(aryl)$_3$ optionally substituted —($C_1$-$C_3$-alkylene)-aryl, optionally substituted —C(O)—$C_1$-$C_6$-alkyl, optionally substituted —C(O)-aryl, —S(O)$_2$—$C_1$-$C_6$-alkyl, optionally substituted —S(O)$_2$-aryl, and optionally substituted —Si($C_{1-6}$alkyl)$_3$.

14. The process of claim 9, wherein the deprotection step is conducted using a Bronsted acid.

15. The process of claim 14, wherein the Bronsted acid is TFA.

16. The process of claim 1, wherein $P^1$ is C(O)—O-tBu.

17. The process of claim 16, wherein the deprotection step is conducted using a Bronsted acid.

18. The process of claim 1, wherein $P^2$ is C(O)—O-tBu.

19. The process of claim 18, wherein the deprotection step is conducted using a Bronsted acid.

* * * * *